United States Patent [19]
Lodhi et al.

[11] Patent Number: 6,043,407
[45] Date of Patent: Mar. 28, 2000

[54] DEBRIDEMENT PAD

[75] Inventors: Shahid Amir Lodhi, Wayne; Josephine Milstone, Ridgefield Park, both of N.J.

[73] Assignee: Warner-Lambert Company, Morris Plains, N.J.

[21] Appl. No.: 09/119,866

[22] Filed: Jul. 21, 1998

Related U.S. Application Data

[60] Provisional application No. 60/054,009, Jul. 29, 1997.

[51] Int. Cl.[7] ........................................... A61F 13/00
[52] U.S. Cl. .................................. 602/48; 602/50; 604/304
[58] Field of Search ................................. 602/41, 50, 48; 604/304

[56] References Cited

U.S. PATENT DOCUMENTS 4,588,400  5/1986  Ring et al. .............................. 604/304

*Primary Examiner*—John G. Weiss
*Assistant Examiner*—Kelvin Hart
*Attorney, Agent, or Firm*—Michael J. Atkins

[57] ABSTRACT

A debridement pad is provided having fibrinolysin enzyme, desoxyribonuclease enzyme and cellulosic material in the form of a lyophilized sponge-like pad. Placement of the pad over an open wound produces a gel which has a protective effect and which releases the enzymes directly into the wound. The pad may also contain antibiotic agents.

14 Claims, No Drawings

DEBRIDEMENT PAD

CROSS-REFERENCE TO RELATED APPLICATION

This application claims priority of U.S. Ser. No. 60/054,009, filed Jul. 29, 1997.

INTRODUCTION

The present invention relates to a debridement pad comprising fibrinolysin, desoxyribonuclease, and a cellulosic polymer.

BACKGROUND OF THE INVENTION

Fibrinolysin is typically employed for enzymatic debridement of necrotic tissue. It is a plasmin-type enzyme which is capable of digesting thrombin Desoxyribonuclease is an enzyme generally used in laboratory research, which catalyzes the hydrolysis or deploymerization of DNA. Enzymatic debridement is the removal of fibrinous or purulent exudate from a wound by the application of a non-toxic and non-irritating enzyme that is capable of lysine, fibrin, denatured collagen, and elastin but which does not destroy normal tissue. Fibrinolysin and desoxyribonuclease are presently used as debriding agents for general surgical wounds, ulcerative lesions, and second and third degree burns. Currently available preparations are in the form of a lyophilized powder and an anhydrous ointment; water-based preparations tend to rapidly lose activity. Powder preparations are associated with significant disadvantages because they require reconstitution prior to use. Once reconstituted, the enzymes exhibit poor storage stability.

SUMMARY OF THE INVENTION

The present invention relates to a composition comprising fibrinolysin, desoxyribonuclease and a cellulosic polymer in the form of a lyophilized pad. The composition of the invention has several advantages over conventional powder and ointment preparations; it is storage stable, and unlike powder preparations, it requires no solubilization prior to use. Since the pad hydrates readily, its placement over an open wound produces a gel which has a protective effect and which releases the comprised enzymes directly into the wound.

DETAILED DESCRIPTION OF THE INVENTION

The present invention relates to a sponge-like lyophilized pad comprising the enzymes fibrinolysin and desoxyribonuclease in combination with a cellulosic polymer or other type of sponge-generating polymers and other compounds such as hylunomic acid salts.

Examples of cellulosic polymers which may be used according to the invention include, but are not limited to lower alkyl containing cellulosic polymers such as hydroxypropylmethyl cellulose, hydroxymethyl cellulose, hydroxypropyl cellulose, hydroxyethyl cellulose, and carboxymethyl cellulose. In preferred embodiments, the cellulosic polymer is hydroxypropylmethyl cellulose, hydroxypropyl cellulose, and hydroxyethyl cellulose.

To prepare a pad according to the invention, one or more of the foregoing cellulosic polymers may be dissolved in water to form a cellulosic solution having a concentration of between about 0.01 and 40 weight percent and preferably between about 0.5 to about 10% weight percent. In specific, nonlimiting embodiments, the concentration of cellulosic polymer may be 1–2 weight percent. Desoxyribonuclease and fibrinolysin may then be added to the cellulosic solution.

The amount of desoxyribonuclease added may be between about 0.1 and 10,000 units per milliliter, and preferably between about 0.1 and 5000 units per milliliter. In particular nonlimiting embodiments of the invention, the ratio of desoxyribonuclease to cellulosic polymer may be 0.1 to 10,000 units per 1–2 grams cellulosic polymer in the pad.

Desoxyribonucleases (DNases) are extra-cellular metabolic products of streptococci of the group A according to Lancefield. Four DNases, which are designated by A, B, C, and D, can be distinguished serologically and electrophoretically. These induce the formation of specific antibodies in humans. Suitable sources of desoxyribonuclease are commercially available from Seravac of Capetown, South Africa.

The concentration of fibrinolysin may be between about 0.05 to 500 units per milliliter, and preferably between about 1 to 250 units/ml units per milliliter. In particular nonlimiting embodiments of the invention, the ratio of fibrinolysin to cellulosic polymer may be about 0.05 to 500 units fibrinolysin per 1–2 grams cellulosic polymer in the pad. Suitable sources of fibrinolysin include bovine, which is commercially available from Warner-Lambert Company, Morris Plains, N.J., USA.

In specific, nonlimiting examples of the invention, the amount of fibrinolysin may be 1–2 units per milliliter and/or the amount of desoxyribonuclease may be 500–1000 units per milliliter of cellulosic solution. Further compounds that may be comprised in the cellulosic solution include, but are not limited to:

antibacterial and antifungel agents including: iodine, povidone iodine, boric acid, sodium borate, oxydale, potassium permanganate, ethanol, isopropanol, formalin, cresol, dimazole, siccanin, phenyliodoundecyncoate, hexachlorophene, resorcin, benzethonin chloride, sodium lauryl sulfate, mercuric chloride, meclocycline, mercurochrome, chlorhexidine gluconate, alkylpolyaminoethylglycine hydrochloride, benzalkonium chloride, nitrofurazone, nystatin, acesulfamin, clotrimazole, sulfamethizole, tolnaftate, pentamycin, amphotericin B, pyrrolnitrin, undecylenic acid, miconazole, trichomycin, variotin, and haloprogin.

antiviral agents including: idoxuridine, trifluridine, viderabine, DDC1, acyclovir, gancyclovir, pyrimethamine, trisulfapyrimidine, flucytosine, AZT;

disrupting DNA metabolism: actinomycin D, doxorubicin, mitomycin C, novobiocin, pilcamycin, rifampin, bleomycin;

inhibiting protein biosynthesis: amikacin, chloramphenicol chloromicitine, clindamycin, erythromycin, oleandomycin, gentamicin, kanamycin, lincomycin, neomycin, netilmicin, paromomycin, spectinomycin, streptomycin, tetracyclines (including tetracycline, oxytetracycline, demeclocycline, doxycycline, methacycline, minocycline), tobramycin, troleandomycin;

altering cellular membrane functions: amphotericin B, colistin, nystatin, polymyxin, griseofulvin;

quinolones including: nalidixic acid, pipemidic acid, cinoxacin, norfloxacin, ciprofloxacin, pefloxacin, fleroxacin, enoxacin, ofloxacin, tosufloxacin, lomefloxacin, stereoisomers of the quinolones;

antimicrobials including: sulfacetamide, sulfisoxazole diolamine, silver sulfadiazine, monovalent and divalent cations, inorganic and organic silver salts, inorganic and organic zinc salts; and antipathogenic polypeptides including: cecropionins, mangainins.

The resulting cellulosic solution may then be sterile filtered and lyophilized using standard techniques to form pads or sheets of sponge-like material, which may optionally be cut to a desired size. Further materials may optionally be added to the pad, such as for example, cotton, a gauze backing, or other support material.

The foregoing method may be performed using sterile techniques, or the pad material may be subsequently sterilized, for example, by radiation.

For use, the pad may be rehydrated shortly prior to use. Suitable solutions for rehydration include, but are not limited to, sterile water, and normal saline. As a specific, nonlimiting example, a pad comprising 0.2 gm cellulosic polymer may be hydrated in a volume of rehydration solution of up to 5 ml for up to 15 minutes. The pad is then removed from the rehydrating solution, and then used to debride a wound, in a subject in need of such treatment, by applying the unhydrated or hydrated pads directly onto the wound. It is desirable to use the rehydrated pad within 2 hours of rehydrating to ensure enzyme activity and to avoid bacterial contamination.

Preferred specific embodiments of the present invention were prepared in the following example.

EXAMPLE

100 Ml cellulosic solutions were prepared according to the above formula comprising either 1% cellulosic or 2% cellulosic polymer. The cellulosic polymer employed was methocel K100 LV form, Dow Chemical. Each solution contained a total of 116 units per ml of fibrinolysin enzyme, bovine (WarnerLambert Company) and 50,000 units per mL of desoxyribonuclease enzyme (Servavac). The solutions were then lyophilized on trays and the resultant sponge pads were packaged at 1.5 grams per package. These packages were assayed for stability. After three months of storage at 37° C., no change in enzyme activity from initial values were noted.

What is claimed is:

1. A debridement pad, comprising fibrinolysis and desoxyribonuclease enzymes in combination with a water-soluble cellulosic polymer.

2. The pad according to claim 1, comprising between about 0.05 and 500 units of fibrinolysin per gram of cellulosic polymer.

3. The pad according to claim 1, comprising between about 0.1 and 10,000 units of desoxyribonuclease per gram of cellulosic polymer.

4. The pad according to claim 2, comprising between about 0.1 and 10,000 units of desoxyribonuclease per gram of cellulosic polymer.

5. The pad according to claim 1, further comprising a compound selected from the group consisting of antibacterial agents, antifungal agents, antiviral agents, analgesics, antimicrobials, antipathogenicpolypeptides, quinolones, inhibitors of protein biosynthesis, and disrupters of DNA metabolism.

6. The pad according to claim 5, wherein the antibiotic is silver sulphadiapine or chloromycitin.

7. The pad according to claim 2, further comprising a compound selected from the group consisting of antibacterial agents, antifungal agents, antiviral agents, analgesics, antimicrobials, antipathogenicpolypeptides, quinolones, inhibitors of protein biosynthesis, and disrupters of DNA metabolism.

8. The pad according to claim 7, wherein the antibiotic is silver sulphadiapine or chloromycitin.

9. The pad according to claim 3, further comprising a compound selected from the group consisting of antibacterial agents, antifuingal agents, antiviral agents, analgesics, antimicrobials, antipathogenicpolypeptides, quinolones, inhibitors of protein biosynthesis, and disrupters of DNA metabolism.

10. The pad according to claim 9, wherein the antibiotic is silver sulphadiapine or chloromycitin.

11. The pad according to claim 4, further comprising a compound selected from the group consisting of antibacterial agents, antifungal agents, antiviral agents, analgesics, antimicrobials, antipathogenicpolypeptides, quinolones, inhibitors of protein biosynthesis, and disrupters of DNA metabolism.

12. The pad according to claim 11, wherein the antibiotic is silver sulphadiapine or chloromycitin.

13. A debridement pad, comprising fibrinolysis and desoxyribonuclease enzymes in combination with a water-soluble cellulosic polymer and prepared by lyophilization.

14. The pad according to claim 13, wherein the water-soluble cellulosic polymer is a lower alkyl cellulosic polymer.

* * * * *